United States Patent [19]

Humphrey et al.

[11] Patent Number: 5,716,970
[45] Date of Patent: Feb. 10, 1998

[54] DIURETIC COMPOUND

[75] Inventors: Stephen J. Humphrey; James T. Curry, both of Kalamazoo; E. Jon Jacobsen, Plainwell, all of Mich.

[73] Assignee: Pharmacia & Upjohn Company, Kalamazoo, Mich.

[21] Appl. No.: 468,129

[22] Filed: Jun. 6, 1995

Related U.S. Application Data

[63] Continuation-in-part of Ser. No. 429,751, Apr. 27, 1995, abandoned.

[51] Int. Cl.[6] .................................................. A61K 31/445
[52] U.S. Cl. .................................................. 514/331
[58] Field of Search .............................. 546/234; 514/331

[56] References Cited

U.S. PATENT DOCUMENTS

| | | | |
|---|---|---|---|
| 3,103,516 | 9/1963 | Schmitt et al. | 546/233 |
| 5,236,921 | 8/1993 | Edmonds et al. | 514/252 |
| 5,350,852 | 9/1994 | Edmonds et al. | 544/336 |

FOREIGN PATENT DOCUMENTS

| | | |
|---|---|---|
| 630887 | 12/1994 | European Pat. Off. . |
| 1112514 | 7/1959 | Germany . |

OTHER PUBLICATIONS

Schmitt, K. et al, Arch. Pharm. 1962, 295, pp. 744–753.

*Primary Examiner*—Bernard Dentz
*Assistant Examiner*—Garth M. Dahlen
*Attorney, Agent, or Firm*—Donald L. Corneglio

[57] ABSTRACT

A diuretic compound of Formula I

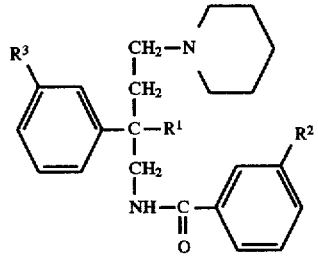

or pharmaceutically acceptable salt thereof where $R^1$ is a $C_{1-6}$ alkyl; $R^2$ is halogen, $C_{1-4}$ alkyl; and $R^3$ is $C_{1-4}$ alkoxy are disclosed, preferably, benzamide, 3-chloro-N-(2-ethyl-2-(3-methoxyphenyl)-4-(1-piperidinyl)butyl), monohydrochloride. The compounds are effective diuretics which increase the excretion of water with little increase in electrolyte excretion.

3 Claims, No Drawings

DIURETIC COMPOUND

CROSS REFERENCE TO RELATED APPLICATIONS

This application is a continuation-in-part of U.S. Ser. No. 08/429,751, filed 27 Apr., 1995, now abandoned.

BACKGROUND OF THE INVENTION

The subject invention is directed toward potent water diuretic pharmaceutical compounds of Formula I. These diuretic compounds are especially useful since they appear to increase urine volume excretion without increasing urinary electrolyte excretion.

Diuretics are useful in the treatment of various medical disorders which result in fluid retention, congestive heart failure, and hypertension. As such these pharmaceutical compounds can be useful in treating the fluid retention and dilutional hyponatremia associated with a number of severe pathologies such as congestive heart failure, chronic liver disease, hepato-renal syndrome, benign and malignant tumors of the lung, liver and central nervous system. Because diuretics are useful in such a large variety of disorders, their use is widespread but complicated by an associated loss of electrolytes such as potassium which is important to carrying out nervous system functions.

A desirable goal is to develop an improved diuretic which effectively increases the excretion of urine without depleting the important electrolytes in the treated patient. The subject pharmaceutical compounds of this invention have this characteristic.

SUMMARY OF THE INVENTION

In one aspect, the subject invention is a compound of structural Formula I:

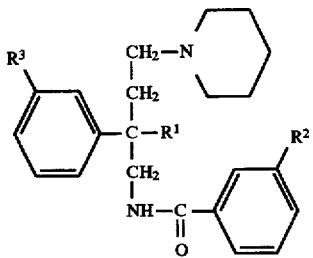

or a pharmaceutically acceptable salt thereof wherein:
$R^1$ is $C_{1-6}$alkyl,
$R^2$ is halogen, $C_{1-4}$ alkyl, and
$R^3$ is $C_{1-4}$ alkoxy.

Preferably, $R^1$ is $C_{1-4}$alkyl or more preferably ethyl; $R^2$ is halogen or chlorine and $R^3$ is methoxy. A particularly preferred compound of Formula I is benzamide, 3-chloro-N-(2-ethyl-2-(3-methoxyphenyl)-4-(1-piperidinyl)butyl), monohydrochloride.

In another aspect, the subject invention is directed toward a method for treating patients suffering from water retention by administering to such a patient a diuretic effective amount of a compound of Formula I as described above. The compound can be administered in a pharmaceutical composition either orally, parenterally or topically. The compound can be administered as a diuretic in an amount of from about 0.15 to about 30 mg/kg of body weight.

DETAILED DESCRIPTION OF THE INVENTION

The invention is a pharmaceutical compound of Formula I, preferably benzamide, 3-chloro-N-(2-ethyl-2-(3-methoxyphenyl)-4-(1 -piperidinyl)butyl), monohydrochloride.

The R groups are as set forth above. As used herein the term $C_{n-m}$ is inclusive such that a compound of $C_{1-6}$ would include compounds of one to six carbons and their isomeric forms. The various carbon moieties are defined as follows: Alkyl refers to an aliphatic hydrocarbon radical and includes branched or unbranched forms such as methyl, ethyl, n-propyl, i-propyl, n-butyl, i-butyl, s-butyl, t-butyl, n-pentyl, i-pentyl, neo-pentyl, n-hexyl, or i-hexyl. Halogen is chlorine, fluorine, bromine or iodide, preferably chlorine.

Both organic and inorganic acids can be employed to form non-toxic pharmaceutically acceptable acid addition salts of the compounds of this invention. Illustrative acids are surfuric, nitric, phosphoric, hydrochloric, citric, acetic, lactic, tartaric, pamoic, ethanedisulfonic, sulfamic, succinic, cyclohexylsulfamic, fumaric, maleic, and benzoic acid. These salts are readily prepared by methods known in the art.

Pharmaceutical compositions of this invention may be prepared by combining the compounds of Formula I with a solid or liquid pharmaceutically acceptable carrier and, optionally, with pharmaceutically acceptable adjuvants and excipients employing standard and conventional techniques. Such pharmaceutical compositions can then be used in treating water retentive states in humans or other warm-blooded animals (patients) by various routes of administration in an effective amount or therapeutically effective amount. Typical amounts can be from about 0.15 to about 30 mg/kg of body weight/day, more preferably, from about 1 to about 10 mg/kg of body weight/day.

Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound of Formula I according to this invention.

The quantity of active component, that is the compound of Formula I according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, water retentive states in warm-blooded animals, the compounds or pharmaceutical compositions thereof will be administered orally and/or parenterally at a dosage to obtain and maintain a concentration, that is, an amount, or blood-level of active component in the animal undergoing treatment which will be effective as a diuretic. Generally, such diuretic effective dosage of active component will be in the range of about 0.15 to about 30, more preferably about 1 to about 10 mg/kg of body weight/day. It is to be understood that the dosages may vary depending upon the requirements of the patient, the severity of the water retention being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3–7. Suitable buffering agents include, for example, trisodium orthophosphate, sodium bicarbonate, sodium citrate, N-methylglucamine, L(+)-lysine and L(+)-arginine to name but a few representative buffering agents. The compound according to Formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned diuretic effective amount of dosage.

Compound of Formula I are patent and effective water diuretics when administered intraperitoneally and orally. The diuretic doses are free of significant overt side effects. Water diuresis is blocked when antidiuretic hormone (ADH; arginine vasopressin) is given prior to or soon after the subject compound's administration. This is indirect evidence that the subject compound's induce water diuresis by suppressing the synthesis or release of endogenous ADH from the posterior pituitary gland. This appears to be a relatively selective effect since it was observed at systemic doses lower than those causing moderate sedation in rats.

Compounds of Formula I have been shown to have opiate binding activity in the CNS receptor binding assay, which is a nonselective assay for affinity for the opiate receptors of the mu (μ), kappa (κ), and delta (δ) subclasses. The drug is also analgesic in several CNS identification assays. Since analgesia is often associated with kappa agonist activity, it is possible that the subject compound's water diuretic and analgesic effects are due to kappa receptor activation.

Compounds of Formula I are very effective agents for shutting off unwanted, excessive, or pathophysiologic ADH release from the posterior pituitary gland. As such, the drug could be very useful in treating the fluid retention and dilutional hyponatremia associated with a number of severe pathologies such as congestive heart failure (CHF), chronic liver disease, hepato-renal syndrome, and benign and malignant tumors of the lung, liver, and central nervous system (CNS). Since ADH also is a very potent vasoconstrictor which may locally act to reduce CNS blood flow, by blocking ADH release, the subject compounds can be effective in improving circulation to the brain and spinal cord in patients who have experienced subarachnoid hemorrhage, stroke, and CNS trauma and concussion. Additionally, by increasing plasma osmolality through its water diuretic action, the drug would tend to reduce osmotically-induced tissue swelling associated with the above-listed CNS diseases and injuries. Third, in milder states of fluid retention such as premenstrual weight gain, the drug could also provide relief. Fourth, while it is unknown if vasoconstriction induced by excess ADH release plays a role in the development or maintenance of hypertension, CHF, and peripheral vascular disease (PVD), it is reasonable to expect that by suppressing ADH, the subject compounds can be antihypertensive and could relax constricted blood vessels in CHF and PVD.

The compounds of the invention can be prepared following the example given below.

EXAMPLE 1

Benzamide, 3-chloro-N-(2-ethyl-2-(3-methoxyphenyl)-4-(1- piperidinyl)butyl), monohydrochloride Sodium amide (8.19 g, 0.210 mol) was added in portions over 30 minutes to a stirred solution of (3-methoxyphenyl) acetonitrile (25.3 g, 0.172 mol) and toluene (100 mL). The reaction was heated in an off bath at 45° for 30 minutes. After cooling to room temperature, a solution of iodoethane (29.5 g, 0.189 mol) and toluene (100 mL) was added over 30 minutes. The internal temperature reached 60° C. during the addition. The solution was heated at reflux for 17 hours before being allowed to cool to room temperature. Aqueous workup (ether, MgSO$_4$, brine wash) and distillation of the residue (84–87° C., 0.1 mm) gave 23.8 g (79%) of a colorless oil: (2-(3'-methoxyphenyl)butyronitrile.

Sodium amide (6.37 g, 0.163 mol) was added in small portions over 20 minutes to the butyl-nitrile (23.8 g, 0.136 mol) in toluene (200 mL). The resultant mixture was heated at 40°–45° C. for 1.5 hours resulting in a deep red-brown solution. After cooling to room temperature, a solution of 1-(2-chloroethyl)piperidine (22.1 g, 0.150 mol) and toluene (100 mL) was added over 25 minutes. The warm mixture was heated at reflux for 2 hours and afterwards the thick slurry was allowed to cool. Concentration and acidic workup (ether, CH$_2$Cl$_2$, MgSO$_4$) provided a brown oil (30.8 g, 79%) sufficiently pure for subsequent reaction.

A sample of the off was converted to the hydrochloride salt and crystallized from CH$_3$OH-ether to give colorless needles (mp 207°–208° C.): (2-Ethyl-2-(3'-methoxyphenyl)-4-piperadino-butyronitrile.

A solution of the nitrile prepared above (5.00 g, 17.5 mmol) in ether (30 ml) was added to a stirred suspension of lithium aluminum hydride (0.800 g, 21.1 mmol) and ether (75 ml). The mixture was stirred at room temperature for 18 hours. Water (0.8 mL), 15% NaOH (0.8 mL) and water (2.4 mL) were added in succession. The residue was stirred for 1 hour, filtered, and the aluminum salts were washed with ether. The filtrates were dried (MgSO$_4$) and concentrated to give a yellow oil (4.80 g, 94%): (2-(3'-methoxyphenyl)-2-(β-piperidinoethyl)butylamine.

A solution of 3-chlorobenzoyl (0.600 g, 3.43 mmol) and ether (30 mL) was added dropwise to a solution of the diamine prepared above (1.00 g, 3.44 mmol), triethylamine (0.38 g) and ether (40 mL) over 5 minutes at 0° C. The resultant suspension was stirred at 0° C. for 1 hour and was allowed to warm to room temperature and stir for 16 hours. Basic workup (ether, NaHCO$_3$, MgSO$_4$, brine wash) and purification by flash chromatography (CHCl$_3$) gave 1.10 g (75%) of the desired product as an oil. An analytical sample was prepared by formation of the hydrochloride salt (ethereal HCl), which was isolated as a white solid (mp eff 120° C.): Benzamide, 3-chloro-N-(2-ethyl-2-(3-methoxyphenyl)-4-(1-piperidinyl)butyl), monohydrochloride.

Biological Data

Example 1 was tested extensively in rat and dog diuretic screening tests. The subject compound proved to be a very potent, effective water diuretic, inducing a 5 to 10 fold increase in urine volumes over the test period without appreciable $Na^+$ or $K^+$ loss.

The general procedures for the staged rat diuretic screen were as follows. Female Harlan Sprague Dawley rats weighing 180 to 250 grams were fasted, given 2 mL of oral saline, dosed i.p. or p.o. with drug or vehicle, and pair-housed in stainless steel metabolism cages. Voided urine was collected from the metabolism cages at 2 and 5 hours post-treatment, the urine volumes were recorded, and aliquots were retained for $Na^+$ and $K^+$ analysis using a NOVA 13 ion-selective electrolyte analyzer. These cation concentrations were then multiplied by their respective urine volumes using an Excel spreadsheet, which calculated 0-2, 2-5, and total 0-5 hour urinary $Na^+$ and $K^+$ excretion. The data was averaged according to drug treatment. Diuretic activity was assigned to those treatments increasing urinary volume excretion by $\geq 50\%$ over the mean of all controls examined during a 2-month report period, and natriuretic activity was assigned to those treatments increasing urinary $Na^+$ excretion by $\geq 50\%$ over the averaged controls. Results for this procedure with Example 1 are shown in Table 1.

A repeat test of Example 1 over lower doses (i.p.) is shown in Table 2.

and analyzed for electrolyte content. Compared to placebo, the subject compound increased urine volume by nearly 3-fold with a slight decline in $Na^+$ elimination. Urinary $K^+$ excretion was unchanged.

What is claimed is:

1. A method for increasing the excretion of urine comprising administering to a patient in need of a diuretic an effective amount of a compound of structural Formula I

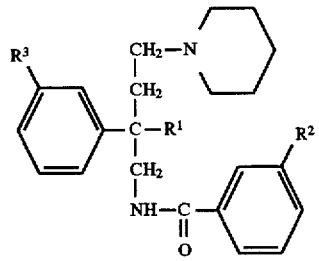

or a pharmaceutically acceptable salt thereof wherein;
$R^1$ is $C_{1-6}$alkyl
$R^2$ is halogen, $C_{1-4}$ alkyl, and
$R^3$ is $C_{1-4}$ alkoxy.

2. A method of claim 1 wherein said compound is benzamide, 3-chloro-N-(2-ethyl-2-(3-methoxypheny)-4-(1-piperdinyl)butyl), monohydrochloride.

TABLE 1

Diuretic Screening of Example 1 in Rats

| i.p. dose (mg/kg) | 0–2 Hour | | | 2–5 Hour | | | 0 . 5 Hour | | |
|---|---|---|---|---|---|---|---|---|---|
| | Vol. (mL) | $Na^+$ (mEq) | $K^+$ (mEq) | Vol. (mL) | $Na^+$ (mEq) | $K^+$ (mEq) | Vol. (mL) | $Na^+$ (mEq) | $K^+$ (mEq) |
| 5.0 | 4.9* | .05ᵃ | .05 | 18.5* | .07ᵃ | .21 | 23.4* | .12ᵃ | .27 |
| 15 | 8.2* | .01ᵃ | .01 | 9.2* | .04ᵃ | .13 | 17.4* | .05ᵃ | .14 |
| 30 | 0.0 | .00ᵃ | .00 | 11.6* | .05ᵃ | .09 | 11.6* | .05ᵃ | .09 |
| Historic Controlᵇ | 1.1 | .10 | .07 | 1.6 | .19 | .12 | 2.7 | .26 | .20 |

*≥50 increase in urinary volume excretion (diuresis)
ᵃ≥50% reduction in urinary $Na^+$ excretion (antinatriuresis)
ᵇaverage of normal control rats not treated with drug

TABLE 2

Repeat Diuretic Screening of Example 1 in Rats

| i.p. dose (mg/kg) | 0–2 Hour | | | 2–5 Hour | | | 0 . 5 Hour | | |
|---|---|---|---|---|---|---|---|---|---|
| | Vol. (mL) | $Na^+$ (mEq) | $K^+$ (mEq) | Vol. (mL) | $Na^+$ (mEq) | $K^+$ (mEq) | Vol. (mL) | $Na^+$ (mEq) | $K^+$ (mEq) |
| 0.15 | 7.9* | .02ᵃ | .05 | 1.3 | .11 | .15 | 9.2* | .13ᵃ | .20 |
| 0.5 | 6.0* | .02ᵃ | .04 | 1.0 | .09ᵃ | .10 | 7.0* | .11ᵃ | .14 |
| 1.50 | 6.6* | .01ᵃ | .01 | 6.7* | .04ᵃ | .24 | 13.3* | .04ᵃ | .24 |
| 5.0 | 4.9* | .02ᵃ | .05 | 20.8* | .03ᵃ | .20 | 25.7* | .05ᵃ | .25 |
| Controlsᵇ | 1.0 | .11 | .07 | 1.4 | .19 | .10 | 2.4 | .30 | .18 |

*≥50% increase in urine volume (diuresis)
ᵃ≥50% decrease in urinary $Na^+$ (antinatriuresis)
ᵇaverage of normal control rats not treated with drug Example 1 compound was tested in conscious dog and exhibited strong diuretic activity, increasing the excretion of water largely independent of electrolyte. The compound was dosed at 1.0 mg/kg orally and urine excretion was collected 3. The method of claim 1 where said effective amount is from about 0.15 to about 30 mg/kg of body weight.

* * * * *